US006815198B2

(12) United States Patent
Nemoto et al.

(10) Patent No.: US 6,815,198 B2
(45) Date of Patent: Nov. 9, 2004

(54) APPARATUS FOR AUTOMATED PREPARATION OF DNA SAMPLES AND REACTOR FOR PREPARING DNA SAMPLES

(75) Inventors: Ryoji Nemoto, Tokyo (JP); Hidemi Yoshida, Tokyo (JP); Hisashi Hagiwara, Tokyo (JP)

(73) Assignee: Hitachi Electronics Engineering Co., Ltd., Tokyo (JP)

( * ) Notice: Subject to any disclaimer, the term of this patent is extended or adjusted under 35 U.S.C. 154(b) by 245 days.

(21) Appl. No.: 09/842,014

(22) Filed: Apr. 26, 2001

(65) Prior Publication Data

US 2001/0036661 A1 Nov. 1, 2001

(30) Foreign Application Priority Data

| Apr. 27, 2000 | (JP) | 2000-127494 |
| Apr. 27, 2000 | (JP) | 2000-127999 |
| Mar. 30, 2001 | (JP) | 2001-098536 |
| Mar. 30, 2001 | (JP) | 2001-099080 |

(51) Int. Cl.[7] .............................................. C12M 1/34
(52) U.S. Cl. ..................... 435/287.2; 435/286.2; 435/286.4; 435/287.3; 435/288.7; 422/82.08; 422/100
(58) Field of Search ................ 435/286.2, 286.4, 435/287.2, 287.3, 288.7; 422/65, 82.08, 100

(56) References Cited

U.S. PATENT DOCUMENTS

| 5,231,029 A | * | 7/1993 | Wootton et al. ............ 422/67 |
| 5,437,979 A | * | 8/1995 | Rampal et al. .......... 435/286.4 |
| 5,656,493 A | * | 8/1997 | Mullis et al. .............. 236/1 C |
| 6,432,719 B1 | * | 8/2002 | Vann et al. ................. 221/131 |
| 2002/0012916 A1 | * | 1/2002 | Gundling et al. ............. 435/6 |

OTHER PUBLICATIONS

Experimental Medicine, vol. 7, No. 2, pp. 14–18, 1989.

* cited by examiner

*Primary Examiner*—David A. Redding
(74) *Attorney, Agent, or Firm*—Mattingly, Stanger & Malur, P.C.

(57) ABSTRACT

An apparatus for automated preparation of DNA samples which comprises a reactor for preparing DNA samples and adjacent thereto an enzyme supply section, a plate holding section, a nozzle sealing section and a cleaning tank section, and wherein plates are loaded onto or unloaded from said plate holding section by means of a transport robot. The reactor for preparing DNA samples comprises a plurality of hollow electroconductive nozzles, hollow syringes coupled to said nozzles and pistons inserted into said syringes, the top of each of said pistons having a piston head secured thereto such that it can move up and down independently of said reactor for preparing DNA samples, the intermediate portions of said electroconductive nozzles being encased in a housing having an opening on both sides, a cooling mechanism being provided adjacent one of said openings, and electroconductive boards being connected to the intermediate portions of the electroconductive nozzles within said housing and also connected to a power supply via conductors.

31 Claims, 13 Drawing Sheets

US 6,815,198 B2

APPARATUS FOR AUTOMATED PREPARATION OF DNA SAMPLES AND REACTOR FOR PREPARING DNA SAMPLES

BACKGROUND OF THE INVENTION

This invention relates to an apparatus for automated preparation of DNA samples that are to be analyzed with a DNA sequencer. More particularly, the invention relates to an automated apparatus with which fluorescence-labelled DNA samples can be prepared with the aid of amplification by thermal cycling, in particular, amplification by polymerase chain reaction (PCR).

A specified DNA region can be amplified at least about $10^5$-fold by repeating DNA synthesis reactions using two primers bracketing that region and a DNA synthetase. This method called polymerase chain reaction (PCR) was developed by the American company Cetus in 1985. It was later modified to use thermostable Taq polymerase and has been established as an efficient PCR-based method. In 1987, another American company Perkin-Elmer and Cetus jointly developed an automated PCR apparatus which contributed to a marked growth of the use of PCR.

Details about the theory of PCR are given in many prior art references. According to Jikken Igaku (Experimental Medicine), Vol. 7, No. 2, pp. 14–18 (1989), the PCR is the sequence of the following three steps: (1) duplex DNA to which primers are joined is thermally denatured to single strands, (2) the primers are annealed and (3) the primed DNA is extended by Taq polymerase. The cycle is repeated several tens of times to amplify the desired DNA fragment.

In the conventional automated PCR apparatus, polymerase chain reaction has been carried out in small test tubes such as plastic Eppendorf tubes which are placed within a chamber that permits temperature control. By changing the temperature in this chamber, the temperature of the reaction mixtures in the Eppendorf tubes is cyclically changed to the levels necessary for (1) denaturation (ca. 94° C.), (2) annealing (ca. 55° C.) and (3) extension (ca. 72° C.).

The conventional automated PCR apparatus can yield only PCR products and their purification, sequencing reaction (for processing the PCR products to prepare samples that can be analyzed with a DNA sequencer) and the purification of the sequencing reaction product cannot be accomplished without a separate apparatus or manual operations.

SUMMARY OF THE INVENTION

An object, therefore, of the invention is to provide an apparatus for automated preparation of DNA samples by which an entire process comprising the preparation of PCR products, their purification, sequencing reaction and the purification of the sequencing reaction product can be performed automatically.

This object of the invention can be attained by an apparatus for automated preparation of DNA samples which comprises a reactor for preparing DNA samples and adjacent thereto an enzyme supply section, a plate holding section, a nozzle sealing section and a cleaning tank section, and wherein plates are loaded onto or unloaded from said plate holding section by means of a transport robot.

Said reactor for preparing DNA samples is supported on a unidirectionally moving mechanism to be capable of moving up and down and comprises a plurality of hollow electroconductive nozzles, hollow syringes coupled to said nozzles and pistons inserted into said syringes, the top of each of said pistons having a piston head secured thereto such that it can move up and down independently of said reactor for preparing DNA samples, the intermediate portions of said electroconductive nozzles being encased in a housing having an opening on both sides, a cooling mechanism being provided adjacent one of said openings, and electroconductive boards being connected to the intermediate portions of the electroconductive nozzles within said housing and also connected to a power supply via conductors.

DETAILED DESCRIPTION OF THE PREFERRED EMBODIMENT

Figure 1:
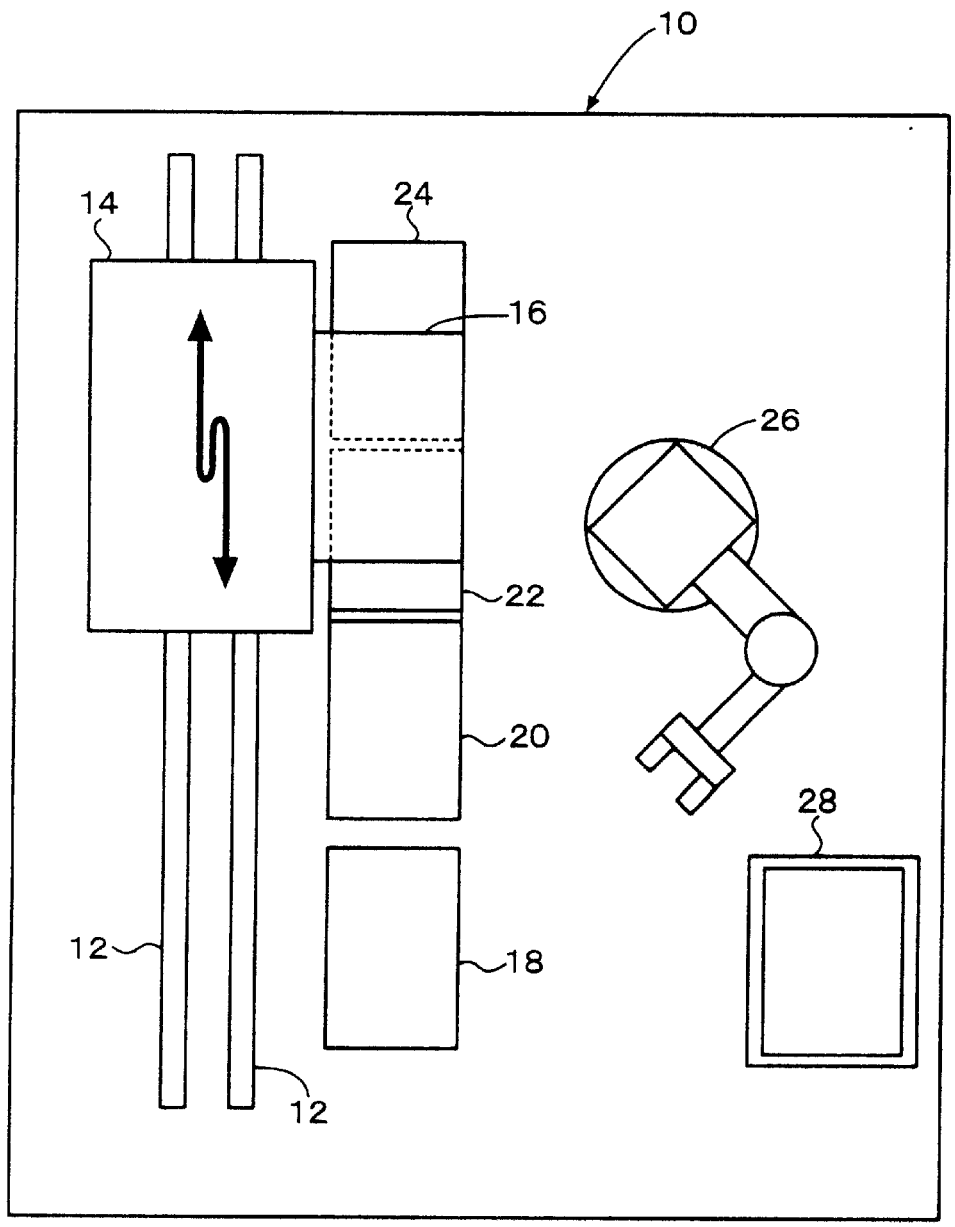
FIG. 1 is a simplified plan view showing an exemplary layout of the apparatus of the invention for automated preparation of DNA samples.

The apparatus of the invention for automated preparation of DNA samples is described below more specifically with reference to the accompanying drawings. FIG. 1 is a simplified plan view showing an exemplary layout of the apparatus. It comprises a horizontal bench 10 carrying two parallel guide rails 12 over which a moving mechanism 14 rests. The moving mechanism 14 is adapted to move along the guide rails 12 in one direction either back and forth or to right and left. A reactor 16 for preparing DNA samples (see below) is fitted to the moving mechanism 14. Parallel to the guide rails 12 are provided an enzyme supply section 18, a plate holding section 20, a nozzle sealing section 22 and a cleaning tank section 24 that are aligned in a straight line. Plates are loaded onto and/or unloaded from the plate holding section 20 by means of a transport robot 26. The plates are if housed in a plate stacker 28.

Figure 2:
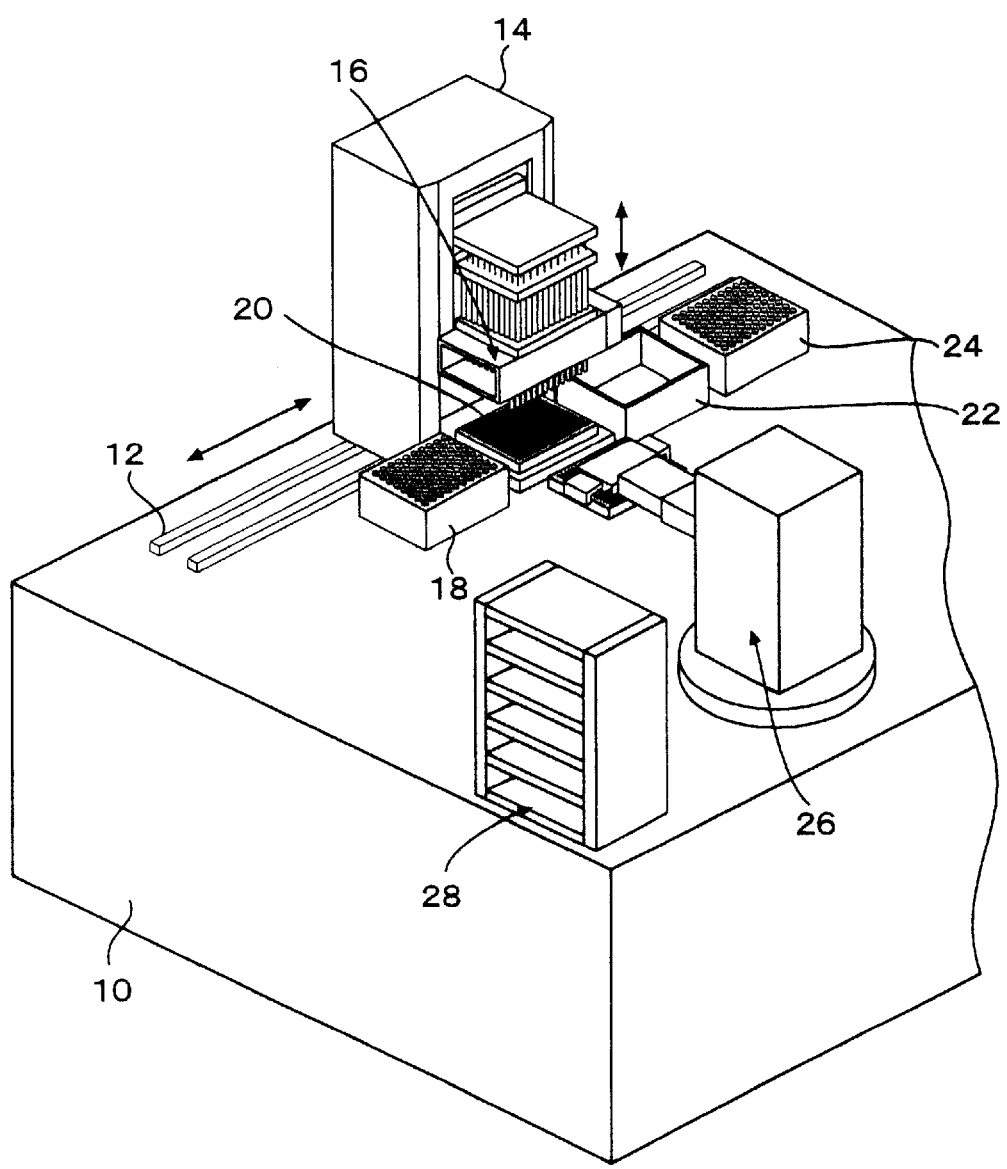
FIG. 2 is a simplified perspective view of the same apparatus.

FIG. 2 is a simplified perspective view of the apparatus shown in FIG. 1. The plate stacker 28 has a plurality of horizontal trays placed one above another and a supply plate or a recovery plate is to be put on each tray. If desired, two dedicated plate stackers may be used, one for supply plates and the other for recovery plates. To start processing, the transport robot 26 picks up a supply plate from one of the trays in the plate stacker 28, carries it to the plate holding section 20 and places it in a predetermined position. The reactor 16 for preparing DNA samples is fitted to the moving mechanism 14 such that it can be moved up and down. The vertically moving mechanism for the reactor 16 may be of a known conventional type such as a stepping motor, a hydraulic mechanism or a ball screw mechanism. If a new plate is put in the plate holding section 20, the moving mechanism 14 moves to this section, moves the apparatus 16 up and down, sucks reagents from within predetermined wells in the plate, further moves to appropriate positions such as the enzyme supply section 18, nozzle sealing section 22 and cleaning tank sections 24 in accordance with a programmed routine, and performs predetermined processing operations which will be described below in detail. When all steps of processing are executed, the transport robot 26 picks up the plate from the plate holding section 20 and puts it back onto a tray for recovery plate in the plate stacker 28.

The operating panel for manipulating the apparatus of the invention for automated preparation of DNA samples, the control unit loaded with programs for controlling various processing actions and other necessary equipment are not shown in FIGS. 1 and 2 but it will be readily understood by the skilled artisan that such operating panel, control unit and equipment are provided as necessary. Needless to say, the horizontal bench 10 of the apparatus of the invention for automated preparation of DNA samples may be covered with a suitable hermetic hood which serves as an effective means for preventing samples and reagents from being contaminated by dust, dirt and suspended miscellaneous germs in air.

Figure 3:
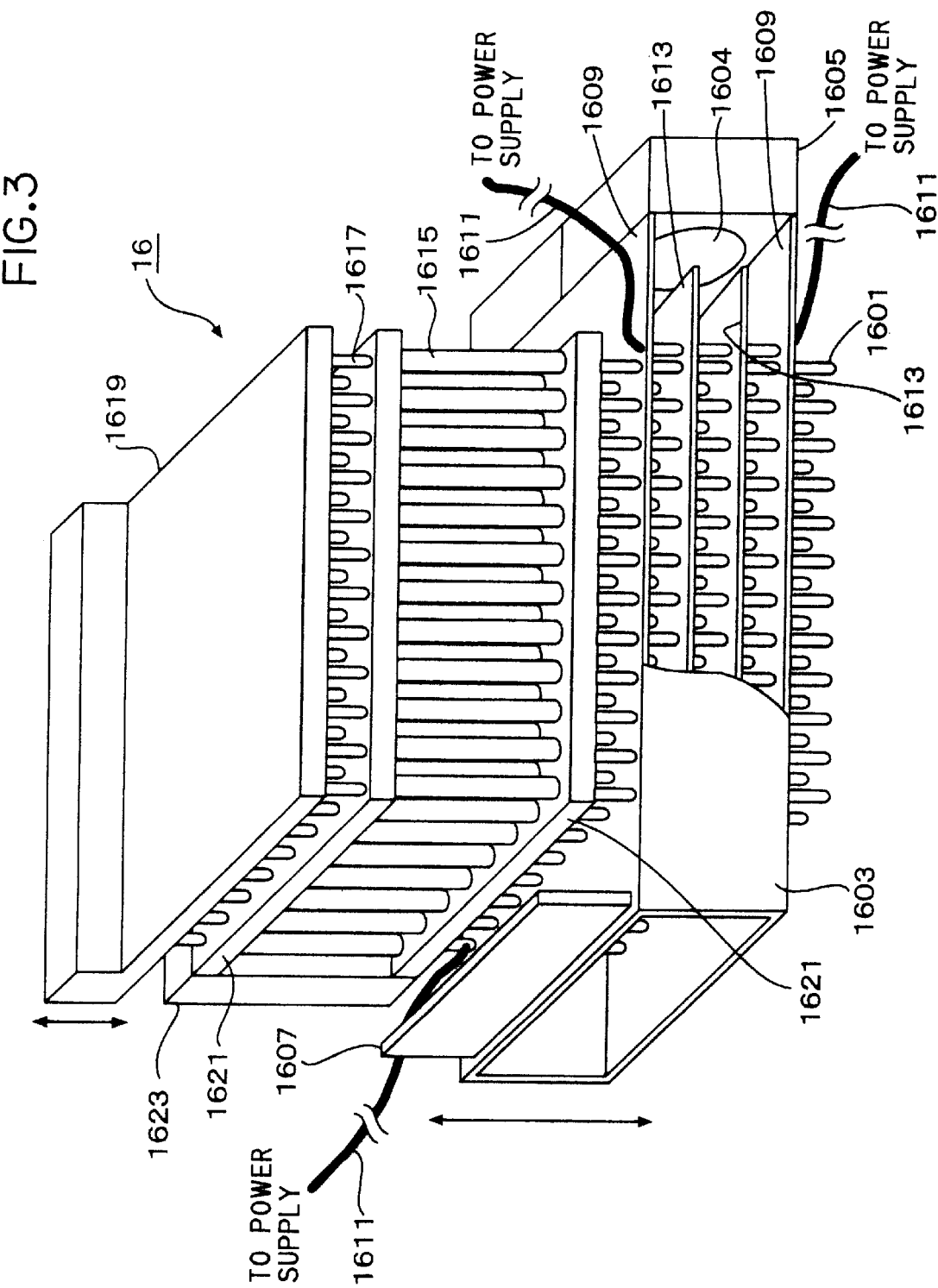
FIG. 3 is a simplified perspective view showing, with part taken away, the reactor for preparing DNA samples which is used in the apparatus of the invention for automated preparation of DNA samples.

FIG. 3 is a simplified perspective view of the reactor 16 which is used in the apparatus of the invention for automated preparation of DNA samples. The reactor 16 has nozzles 1601 extending from the bottom that are made of a conductive material, say, stainless steel. The nozzles 1601 are typically 96 in number but their number is variable. The intermediate portions of the nozzles 1601 are encased in a housing 1603 that can be rendered hermetic. At one end of the housing 1603 is provided a cooling mechanism (e.g. air-cooled fan) 1605 having a shutter 1064 that can be slid open. A shutter 1607 that can be slid open is also provided at the other end of the housing 1603. Nozzles 1601 are connected to two conductive boards 1609, one in the upper part and the other in the lower part. The conductive boards 1609 are typically made of copper or stainless steel. The area defined by the two conductive boards 1609 is the heating zone for the nozzles 1601. The housing 1603 may remain open at both ends.

In this case, there is no need to provide the shutters 1604 and 1607 but the air-cooled fan 1605 without shutter is provided adjacent one open end of the housing 1603.

Conductor cables 1611 extending from a power supply (not shown) are connected to the conductive boards 1609. If the power supply is turned on, an electric current flows from the conductive boards 1609 to the individual conductive nozzles 1601, which are heated by Joule's heat. Conversely, if the power supply is turned off, the heating of the nozzles 1601 ends and both the shutter 1604 on the air-cooled fan 1605 and the shutter 1607 are slid open and the air-cooled fan 1605 is driven to cool the nozzles 1601. Plates 1613 are provided between the conductive boards 1609 for straightening the air streams created by the fan 1605 so that the nozzles 1601 are effectively cooled within a short time. Two straightening plates are shown in FIG. 3 but three or more straightening plates may be provided. The straightening plates 1613 are typically made of ceramics, copper, plastics or stainless steel.

The nozzles 1601 are coupled to syringes 1615. Pistons 1617 are inserted into the syringes and a vertically movable piston head 1619 is securely fixed to the pistons 1617 at the top. The piston head 1619 is supported on an independent vertically moving mechanism (not shown) which can be operated independently of the vertically moving mechanism for the overall operation of the reactor 16. The vertically moving mechanism for the piston head 1619 may also be of a known conventional type such as a stepping motor, a hydraulic mechanism or a ball screw mechanism.

The syringes 1615 are fixed to two fixing plates 1621, one at the top and the other on the bottom. The fixing plates 1621 are securely fixed to a mounting plate 1621 at an end. The mounting plate 1621 is attached to the vertically moving mechanism (not shown) in the moving mechanism 14 so as to secure the vertical movements of the reactor 16. As already mentioned, the piston head 1619 is attached to the other independent vertically moving mechanism (not shown) in the moving mechanism 14 so as to secure the vertical movements of the pistons 1617.

Figure 4:
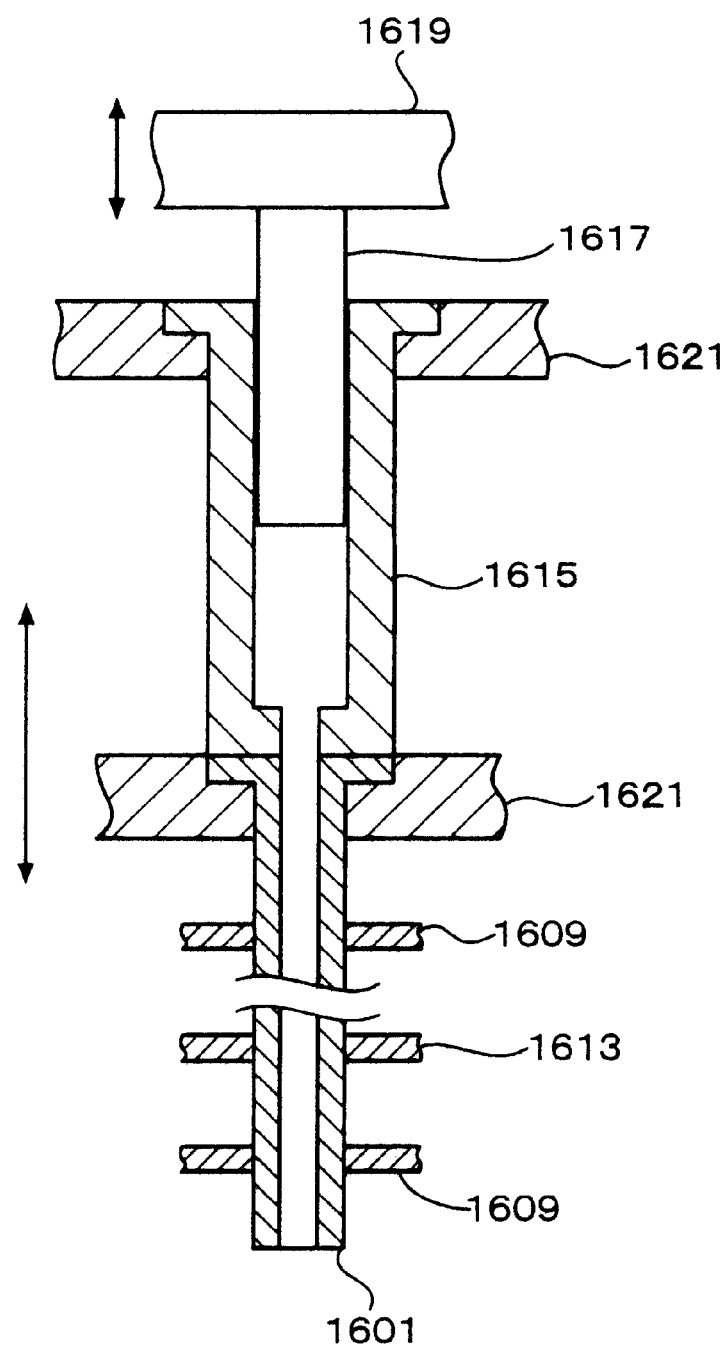
FIG. 4 is a simplified partial sectional view showing how nozzles, syringes and pistons are assembled for integration in the reactor shown in FIG. 3.

FIG. 4 is a partial enlarged sectional view showing how nozzles 1601, syringes 1615, pistons 1617 and piston head 1619 are assembled as an integral unit. As already mentioned, the nozzles 1601 are made of stainless steel but they can also be made of other conductive materials including copper, aluminum, gold and platinum. The nozzles 1601 are preferably coated with Teflon on both inner and outer surfaces. Each of the nozzles 1601 may typically have an outside diameter of 1.27 mm, an inside diameter of 0.8 mm and an overall length of 100 mm. With this size, each nozzle 1601 has an internal volume of ca. 60 $\mu$L which is sufficient for carrying out PCR and sequencing reactions. All reactions involved in PCR and sequencing are carried out within these nozzles 1601. Hence, the nozzles 1601 serve as vessels in which to carry out the PCR and sequencing reactions.

The constituent material for the fixing plates 1621 is not limited to any particular type but they are preferably made of materials having both electrical insulating and heat resisting properties as exemplified by ceramics and plastics. They may of course be formed of metals. Similarly, the constituent material for the syringes 1615 is not limited to any particular type but they are preferably formed of materials having both electrical insulating and heat resisting properties as exemplified by glass and plastics. They may of course be formed of metals. The pistons 1617 are preferably made of glass or plastics. Alternatively, the syringes 1615 and the nozzles 1601 may be formed of the same metallic material (e.g. stainless steel) so that they can be rendered monolithic.

Figure 5:
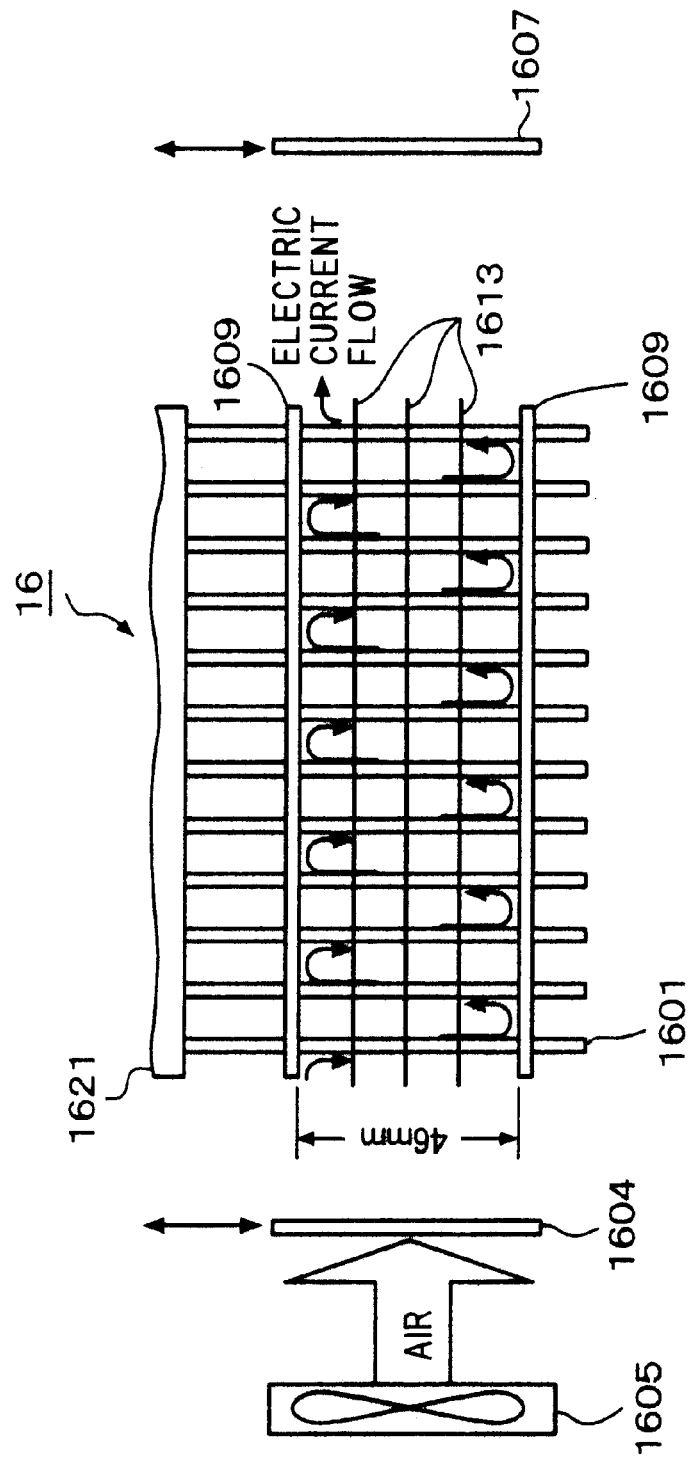
FIG. 5 is a schematic simplified view showing how the nozzles in the reactor shown in FIG. 3 are heated and cooled.

FIG. 5 is a schematic simplified view showing how to heat and cool the nozzles 1601. The heating zone for the nozzles 1601 is defined by the two conductive boards 1609 which are spaced apart by a distance of 46 mm. The 96 nozzles are wired in series and connected between the two conductive boards 1609. A dc voltage of 35.4 V (up to 43 V) is applied to produce a current of 8.2 A (up to 10 A). The heating time is 5 seconds (as calculated for heating up to 50° C.). These values assume that the nozzles used have an outside diameter of 1.27 mm and an inside diameter of 0.8 mm, are made of SUS 304 having and are heated over a distance of 46 mm. If other nozzle conditions are used, the voltage, current and heating time will have different values. The skilled artisan can readily determine the appropriate values of voltage, current and heating by repeated experiments. To secure appropriate temperature control, a temperature sensor such as a thermocouple (not shown) is preferably provided at suitable sites in the heating zone. As already mentioned, when the nozzles are heated, the shutters 1604 and 1607 are closed to shut off the nozzle heating space. In this case, air-cooled fan 1605 also stops operating. To cool the nozzles, voltage application is stopped and at the same time the shutters 1604 and 1607 are slid open and air-cooled fan 1605 is driven so that ambient air is blown against the outer surfaces of the nozzles.

Figure 6:
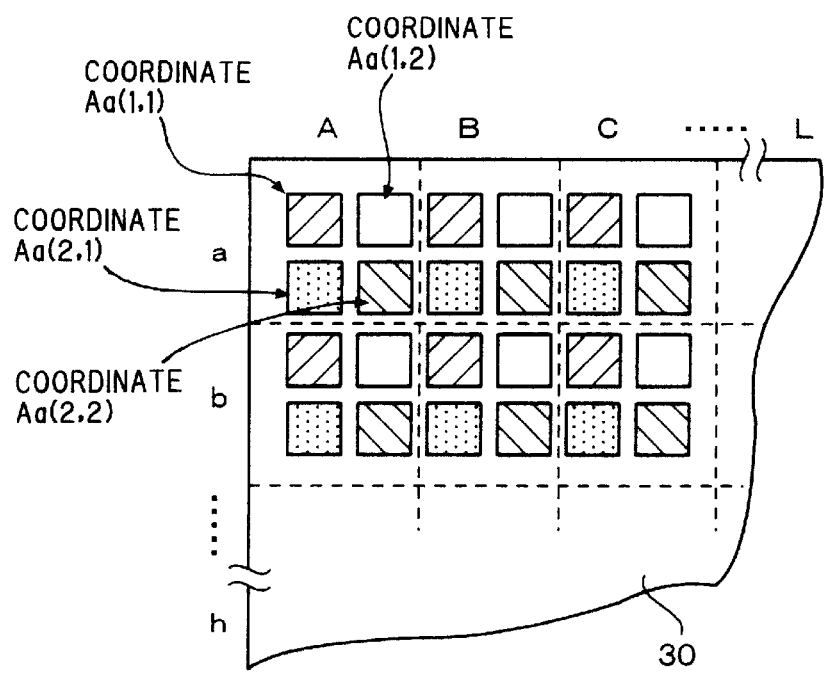
FIG. 6 is a partial enlarged schematic view of a plate to be used in the apparatus of the invention for automated preparation of DNA samples.

The plates to be used in the apparatus of the invention for preparing DNA samples are common microtiter plates having a plurality of concavities or wells in the top surface. The plates may be formed of any suitable materials such as ceramics, glass and plastics. FIG. 6 is a partial simplified plan view of a microtiter plate 30 having 384 wells. Since every four wells are used to perform PCR and sequencing reactions, the plate 30 has 96 divisions consisting of 8 divisions a–h on the vertical axis and 12 divisions A–L on the horizontal axis. At coordinate Aa, there are four wells specified by (1,1), (1,2), (2,1) and (2,2) which are filled with the necessary reagents that are used at the respective stages of processing. For example, well (1,1) is filled with the reaction mixture and primers used in the first step of PCR; well (2,1) is used as a reaction well; well (1,2) is filled with a sequencing primer; and well (2,2) is filled with a sequencing reaction mixture. Amplification by PCR can be performed using a reaction mixture kit commercially available from Perkin-Elmer. The kit is a 30-$\mu$L solution consisting of 3 $\mu$L DNA template (e.g. ca. 200 ng human genome), 3 $\mu$L 10×PCR buffer, 3 $\mu$L (2.5 mmol) dNTP, 3 $\mu$L (10 $\mu$mol) primer 1, 3 $\mu$L (10 $\mu$mol) primer 2, 0.2 $\mu$L Ex Taq and 15 $\mu$L H$_2$O. Other reaction mixtures and primers can of course be used. The wells at the other coordinates Ab–Ah, Ba–Bh, Ca–Ch, . . . , La–Lh are filled with the same reagents as placed in the wells (1,1), (1,2), (2,1) and (2,2). Other reagents may of course be put in these wells. Depending on the use, the wells may be grouped in twos, threes, etc.

Figure 7:
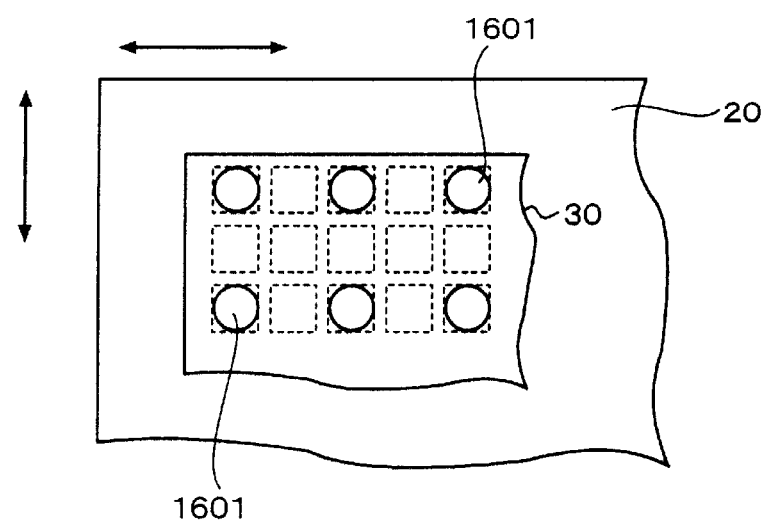
FIG. 7 is a partial enlarged schematic view showing the plate of FIG. 6 into which some nozzles have been inserted.

As FIG. 7 shows, in order to insert a nozzle 1601 into either one of the wells (1,1), (1,2), (2,1) and (2,2) that is determined by the specific step of processing, the plate 30 is moved in X-Y direction as it rests on the plate holding section 20. Movement of the plate 30 in X-Y direction can be realized by adapting the plate holding section 20 to be movable in X-Y direction; the same result can be attained by allowing the arm of the transport robot 26 to hold the plate 30. Alternatively, the nozzle 1601 itself may be moved in X-Y direction.

Figure 8:
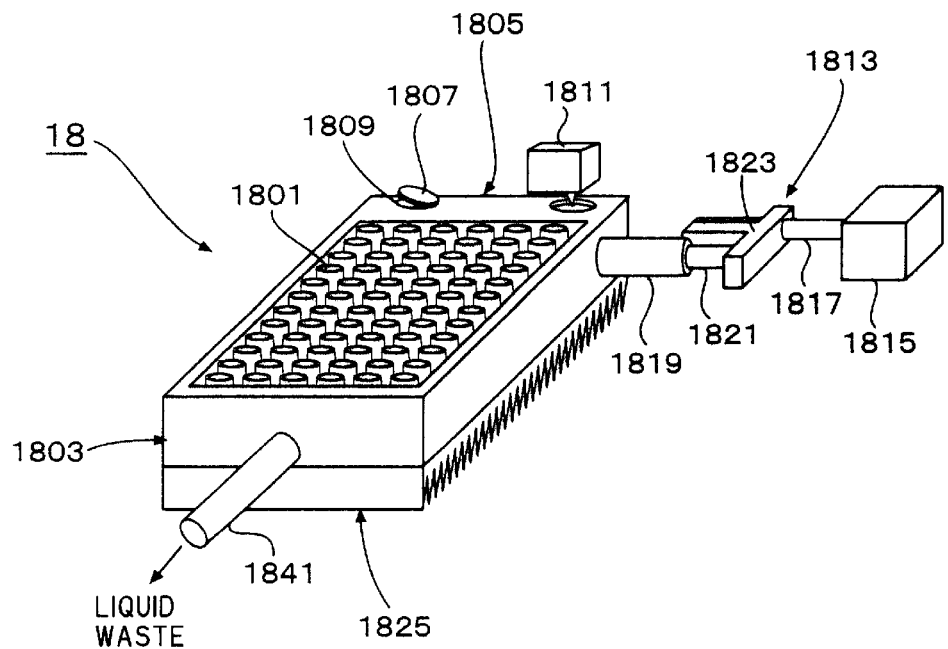
FIG. 8 is a simplified perspective view of the enzyme supply section which is used in the apparatus of the invention for automated preparation of DNA samples.

FIG. 8 is a simplified perspective view of an exemplary structure of the enzyme supply section 18 where the enzymes used in PCR and which remain unreacted are decomposed and purified. In the process of sample preparation, a centrifuge is conventionally used to purify the PCR amplified products. The apparatus of the invention allows for full automation of PCR and sequencing reactions by using enzymes. Two enzymes are used; one is alkaline phosphatase shrimp (APS) for removing unreacted dNTP and the other is exonuclease I (ExoI) for removing unreacted primers. Other decomposing enzymes may of course be used. Each of these enzymes is diluted 20-fold with, for example, TE and supplied in portions of a predetermined quantity, say, 2 $\mu$L. The enzyme supply section 18 comprises basically a rectangular container 1803 with its top open and a closed enzyme tank 1805 coupled monolithically to it. The container 1803 has a plurality of, say, 96, enzyme supply pots 1801 erected on the bottom. An enzyme solution is supplied through an inlet 1809 that is formed in the top surface of the enzyme tank 1805 and which is fitted with an openable lid 1807. The enzyme solution can be supplied by any suitable means that is not shown in FIG. 8 or it may be supplied manually by operating personnel. The enzyme tank 1805 is preferably provided with a level sensor 1811 for detecting how much of the enzyme solution is left in the tank 1805. The supply of the enzyme solution into the tank 1805 is controlled in response to a detection signal from the level sensor 1811.

The enzyme supply section 18 also has a solution transfer mechanism 1813 for transferring the enzyme solution from the enzyme tank 1805 into the enzyme supply pots 1801. The solution transfer mechanism 1813 typically uses a stepping motor 1815 which rotates a precision feed screw 1817 so that a piston 1821 is moved back and forth through a syringe 1819. The precision feed screw 1817 and the piston 1821 are coupled by a connecting arm 1823.

Decomposition enzymes such as alkaline phosphatase shrimp (APS) and endonuclease I (ExoI) are occasionally deactivated at elevated temperatures. To deal with this possibility, the bottoms of the rectangular container 1803 and the enzyme tank 1805 are entirely covered with a cooling unit 1825. Preferably, the cooling unit 1825 maintains the enzyme solution at about 4° C. which is low enough to keep the enzymes dormant.

Figure 9:
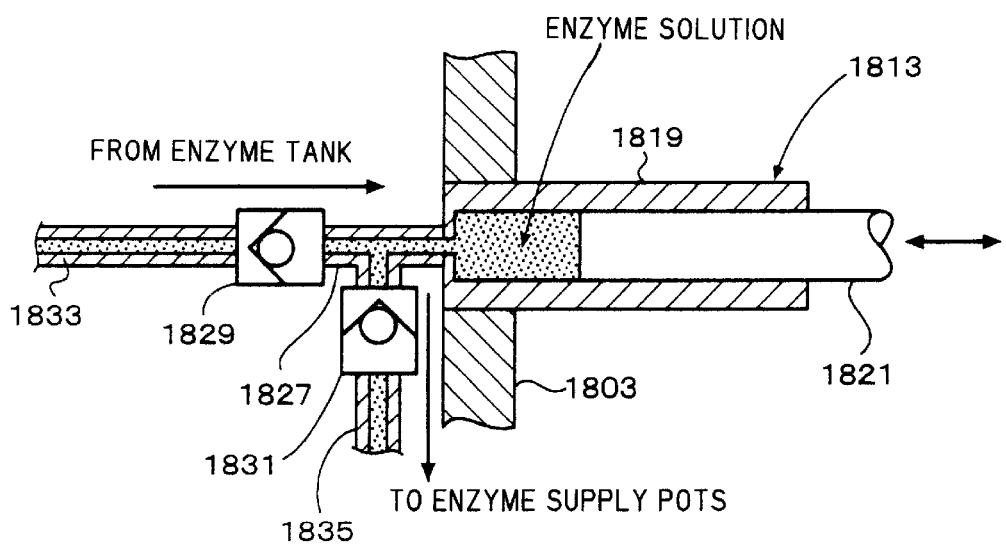
FIG. 9 is a partial enlarged section of the solution transfer mechanism provided in the enzyme supply section shown in FIG. 8.

FIG. 9 is a partial enlarged section of the solution at transfer mechanism 1813 shown in FIG. 8. A generally T-shaped pipe 1827 is connected to the distal end of the syringe 1819. A check valve 1829 is connected to an end of the T pipe 1827 and another check valve 1831 is connected to the other end of the T pipe. The other end of the check valve 1829 is connected to a pipe 1833 from the enzyme tank 1805; the other end of the check valve 1831 is connected to a pipe 1835 branching into the enzyme supply pots

1801. If the piston 1821 is pulled, the enzyme solution from the enzyme tank 1805 passes through the check valve 1829 to fill the syringe 1819. On this occasion, the check valve 1831 remains closed, so the enzyme solution will not flow into the enzyme supply pots 1801. If the piston 1821 is pushed in, the enzyme solution in the syringe 1819 passes through the check valve 1831 to be transferred into the enzyme supply pots 1801. On this occasion, the check valve 1829 remains closed, so the enzyme solution in the syringe 1891 will not return to the enzyme tank 1805.

Figure 10:
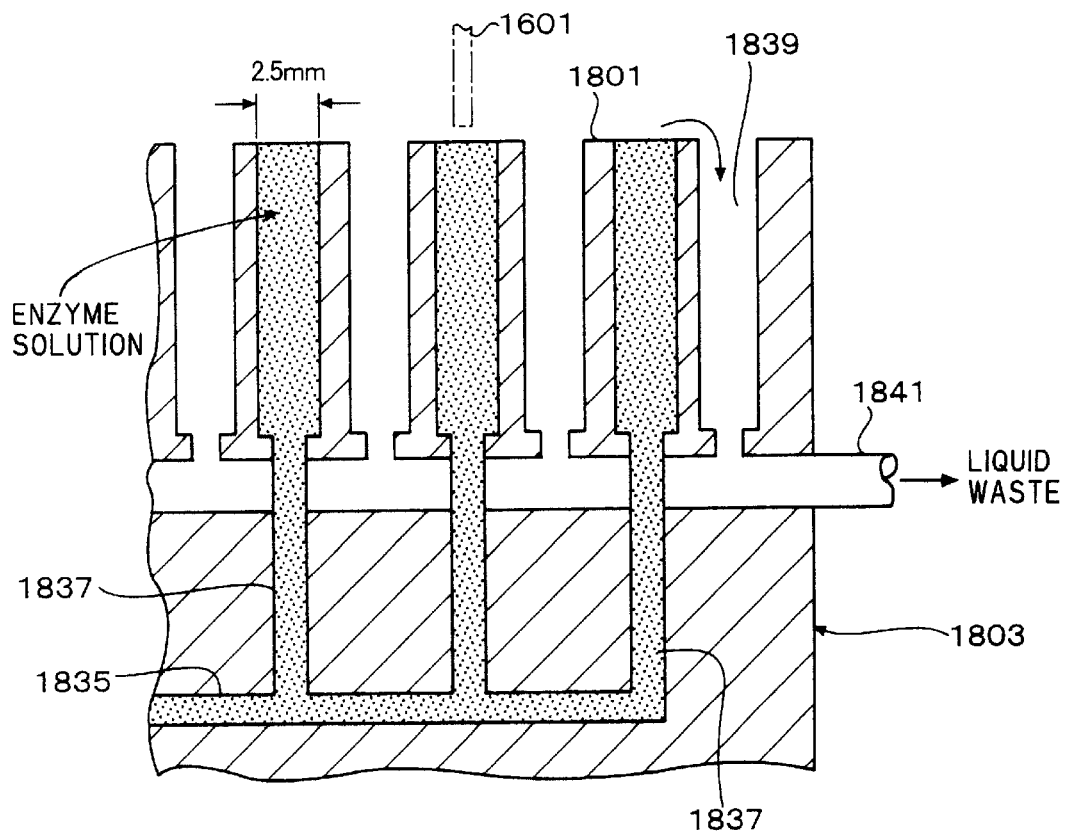
FIG. 10 is a partial enlarged section of enzyme supply pots provided in the enzyme supply section shown in FIG. 8.

FIG. 10 is a partial enlarged section of enzyme supply pots 1801. The pipe 1835 branches in supply pipes 1837 which are connected to the bottoms of the enzyme supply pots 1801. If the piston 1821 is pushed in, the enzyme solution in the syringe 1819 passes through the check valve 1831 and flows through the pipe 1835 and branch pipes 1837 until it fills up the pots 1801 from bottom to top. If a nozzle 1601 is inserted into the pot 1801, the enzyme solution in the pot 1801 may occasionally overflow; the overflowing enzyme solution falls into an emission space 1839 adjacent each pot 1801 and thereafter flows through a liquid waste drain 1841 to be discarded to the outside of the container 1803.

Figure 11:
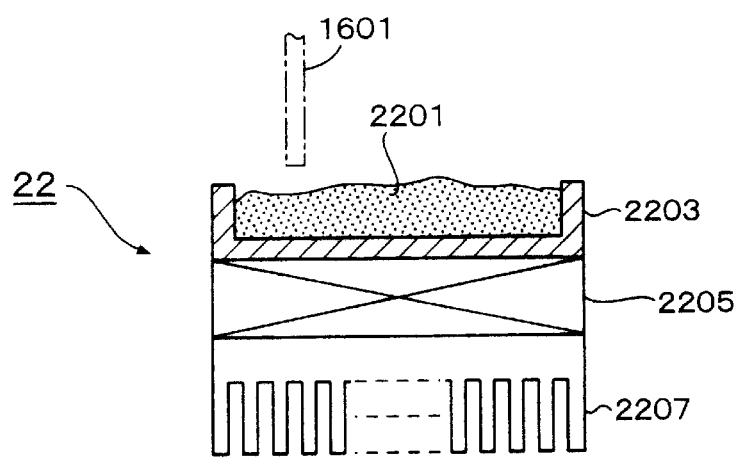
FIG. 11 is a simplified sectional view showing an exemplary structure of the nozzle sealing section which is used in the apparatus of the invention for automated preparation of DNA samples.
Figure 12A:
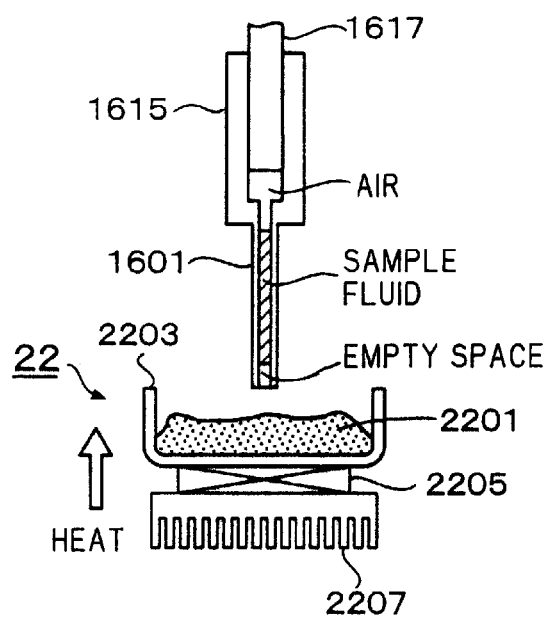
FIG. 12A shows schematically a nozzle in the nozzle sealing section which is about to be inserted into a heated paraffin bath.
Figure 12B:
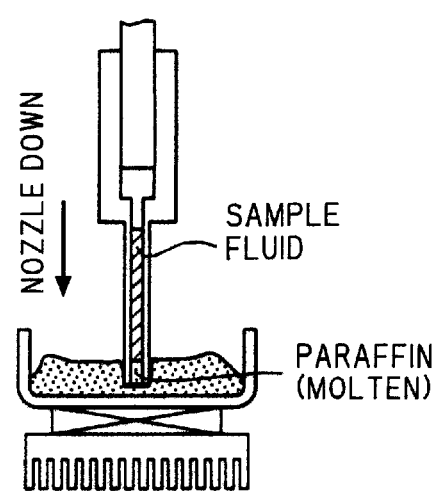
FIG. 12B shows schematically the nozzle as it has been inserted into molten paraffin.
Figure 12C:
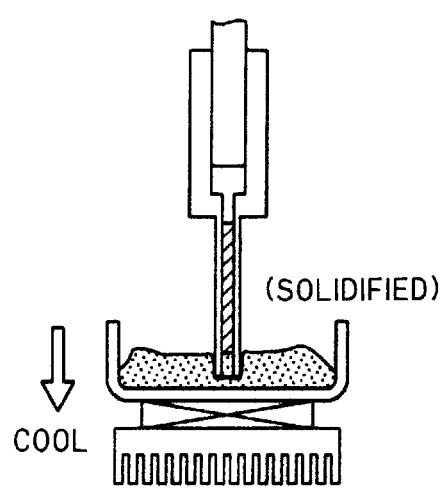
FIG. 12C shows schematically the nozzle as it has been sealed by solidified paraffin.
Figure 12D:
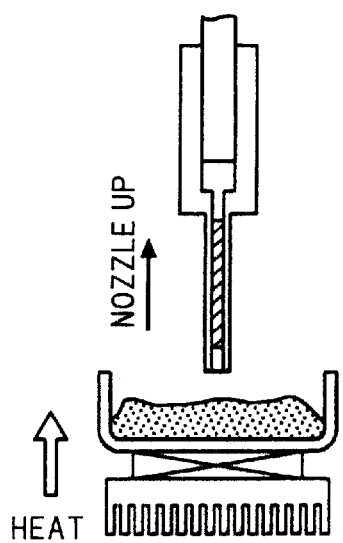
FIG. 12D shows schematically the nozzle as it has been withdrawn from remelted paraffin.

FIG. 11 is a simplified sectional view showing an exemplary structure of the nozzle sealing section 22. As shown, the nozzle sealing section 22 comprises a tray 2203 filled with paraffin 2201, a heating/cooling means 2205 bonded to the underside of the tray 2203, and a heat sink 2207 bonded to the other side of the heating/cooling means 2205. It should be noted that the heat sink 2207 is not essential to the present invention. The heating/cooling means 2205 is typically a Peltier device.

If thermal cycles are applied to the sample reaction liquor in a conductive nozzle 1601 (see FIG. 4) so as to perform PCR and sequencing reactions in the nozzle, air bubbles within the nozzle can expand at elevated temperatures and the sample reaction solution may be ejected out of the nozzle. In order to avoid this problem, the tip of the conductive nozzle 1601 is sealed with paraffin 2201 before thermal cycling starts. This paraffin sealing has enabled all PCR and sequencing reactions to be performed in a fully automatic manner.

FIG. 12 shows schematically the sequence of steps in paraffin sealing. In step A, the Peltier device 2205 is driven to heat the tray 2203 so that the paraffin in the tray 2203 is melted. The piston 1617 is lifted up only a little to form an empty space at the tip of the nozzle 1601 which is filled with the sample solution. In step B, the nozzle 1601 is lowered down so that its tip is immersed in the molten paraffin, whereupon the paraffin 2201 gets into the empty space at the tip of the nozzle 1601. In step C, the Peltier device 2205 is driven in reverse direction to cool the tray 2203 so that the paraffin in the tray 2203 is solidified, whereupon the tip of the nozzle 1601 is completely sealed with the paraffin. With the paraffin bath 2203 being cooled with the Peltier device 2205 (to keep the paraffin 2201 solidified), an electric current is flowed through the nozzle 1601 as shown in FIG. 5 (with its tip paraffin-sealed) so that it is heated to the temperature necessary for performing PCR or sequencing reactions and a predetermined reaction is carried out within the nozzle; thereafter, the application of the current is stopped, the nozzle 1601 is cooled and a predetermined thermal cycle is repeated. Since the tip of the nozzle 1601 is not heated, the paraffin seal is not melted but remains solidified. If the predetermined thermal cycle is repeated to complete the necessary PCR or sequencing reactions, the process goes to step D, in which the Peltier device 2205 is driven to heat the tray 2203 so that the paraffin in the tray is melted. If the paraffin 2201 is completely melted, the nozzle 1601 is lifted up from the tray (paraffin bath). Since the paraffin sealing the tip of the nozzle 1601 is also melted, the tip of the lifted nozzle 1601 returns to the initial emptiness (see step A). As already mentioned, the nozzle 1601 is coated with Teflon on both the inner and outer surfaces, the liquid paraffin can be readily removed from the tip of the nozzle 1601.

Figure 13:
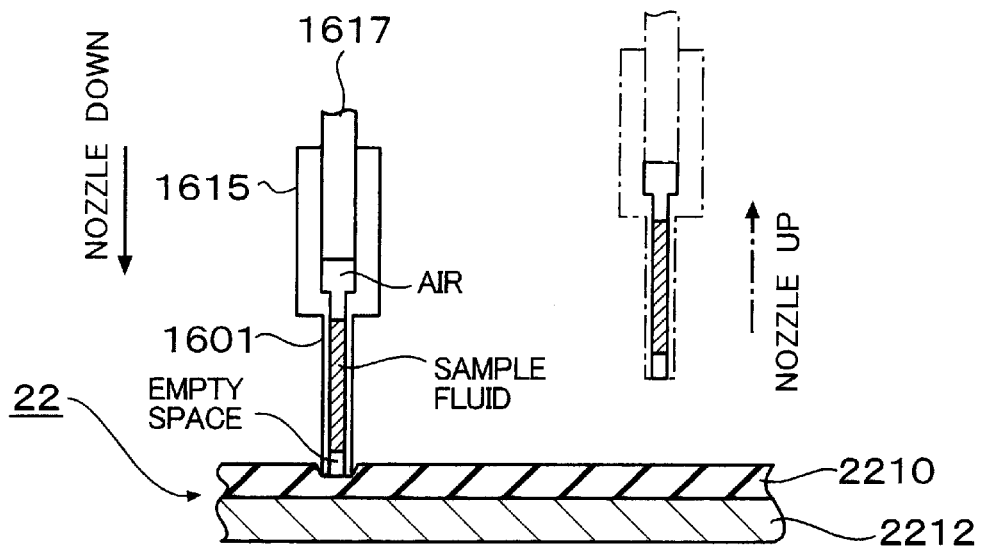
FIG. 13 is a simplified sectional view showing another exemplary structure of the nozzle sealing section which is used in the apparatus of the invention for automated preparation of DNA samples.

Alternatively, the tip of the nozzle 1601 may be pressed onto the surface of a mat which is indicated by 2210 in FIG. 13 and this produces the same result as the paraffin sealing strategy illustrated in FIGS. 11 and 12. To be more specific, the tip of the nozzle 1601 which is not filled with the sample solution is pressed onto the mat 2210 and with it remaining in this state, an electric current is flowed through the nozzle 1601 so that it is heated to the temperature necessary for performing PCR or sequencing reactions and a predetermined reaction is carried out within the nozzle; thereafter, the application of the current is stopped, the nozzle 1601 is cooled and a predetermined thermal cycle is repeated. Since the empty space at the tip of the nozzle 1601 has the necessary and sufficient capacity, the sample will not be ejected out of the nozzle even if it is heated to expand. If the predetermined thermal cycle is repeated to complete the necessary PCR or sequencing reactions, the nozzle 1601 is lifted up from the surface of the mat 2210 and moved to the next step of processing. In FIG. 13, reference numeral 2212 designates the support of the mat 2210.

Figure 14:
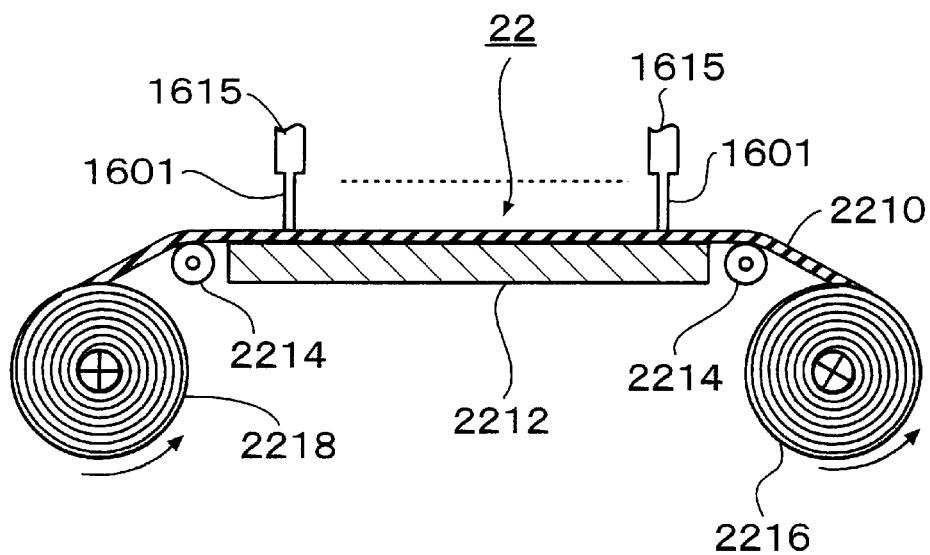
FIG. 14 is a simplified sectional view showing an embodiment in which a continuous web of sheet is used as the mat in the nozzle sealing section shown in FIG. 13.

If the tip of a different nozzle 1601 is pressed onto the surface of the mat 2210 at the same site as where the previous nozzle was pressed to seal its tip, contamination might occur. To avoid this risk, the tip of a nozzle 1601 for performing a second cycle of PCR amplification must always be pressed onto the mat 2210 at a site that has not been used before. To meet this requirement, the mat 2210 is preferably moved back and forth and/or to right and left by a known conventional means (not shown). The mat may be sheet fed so that it is replaced by a new one at each end of the entire process of PCR amplification. If desired, a web of continuous sheet may be delivered little by little for each process of PCR amplification. In FIG. 14, reference numeral 2214 designates a tension roll, 2216 is a delivery roll, and 2218 is a take-up roll. By using the device shown in FIG. 14, the position of the mat is changed at each end of the process of PCR amplification and there is no possibility that the PCR amplified products will contaminate the next process of PCR amplification. As a result, the apparatus of the invention for preparing DNA samples can be run continuously for extended periods.

Being used for the stated purpose, the mat 2210 can be formed of materials that are heat resistant, flexible, elastic and non-conductive. Preferred examples of such materials include fluoroplastics, fluororubbers, urethane rubber, silicone rubber and chloroprene rubber. It is generally preferred that the mat has a thickness in the range of 1.0–10 mm. If the mat is thinner than 1.0 mm, the tip of the nozzle cannot be adequately sealed and, in addition, the mat may be broken by the tip of the nozzle. If the mat is thicker than 10 mm, the effect of sealing the tip of the nozzle is saturated and diseconomy results; in addition, such a thick mat is difficult to handle. Particularly in the case of using the web of continuous sheet shown in FIG. 14, the mat thickness is preferably in the range of 1.0–5.0 mm.

Figure 15:
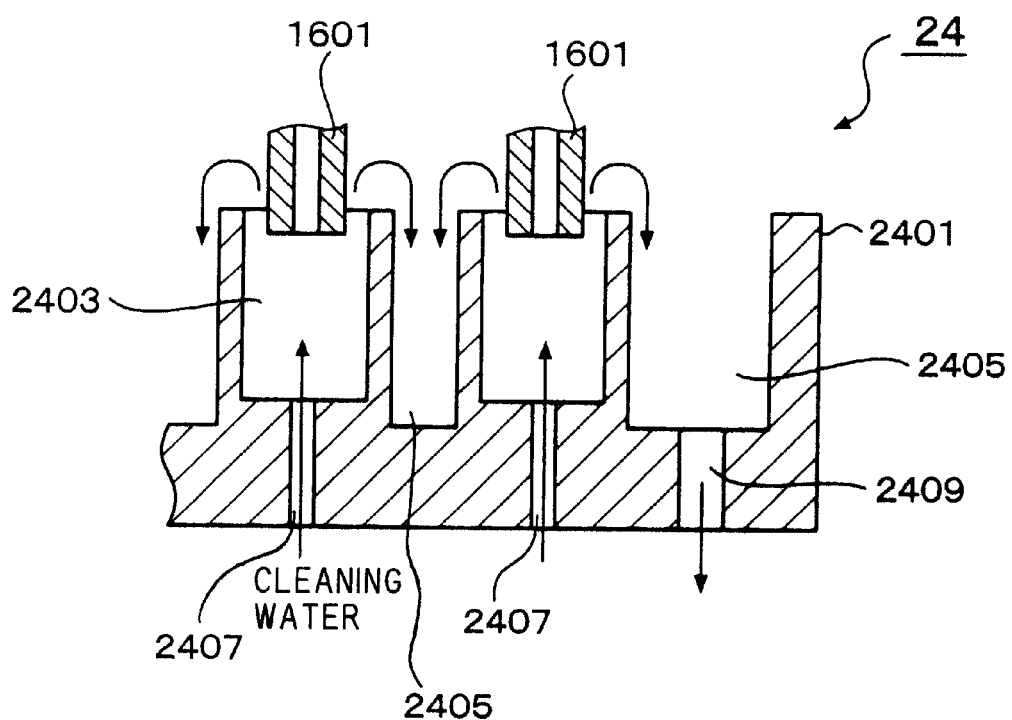
FIG. 15 is a partial simplified sectional view showing an exemplary structure of the cleaning tank section which is used in the apparatus of the invention for automated preparation of DNA samples.

FIG. 15 is a partial simplified sectional view showing an exemplary structure of the cleaning tank section 24. As shown, the cleaning tank section 24 consists of a cleaning tank 2401 which contains in it a plurality of cleaning pots 2403 of a specified height and a plurality of drain trenches 2405. The cleaning tank 2401 may have a rectangular shape. The bottom of each cleaning pot 2403 communicates with a cleaning water inlet 2407. The cleaning water may be selected from various kinds of impurity-free water such as pure water, deionized water and distilled water. A suitable pipe or the like may be provided between a supply source of cleaning water (not shown) and each of the cleaning water inlets 2407. The capacity of each cleaning pot 2403 is preferably the same as or slightly greater than the internal volume of the nozzle. During the cleaning process, the cleaning pots 2403 are preferably kept supplied with fresh cleaning water so that it keeps overflowing these cleaning pots. While the fresh cleaning water keeps overflowing the cleaning pots 2403, the tip of a nozzle 1601 is immersed into the cleaning water from above the cleaning pot 2403. When the piston 1617 is advanced into the cleaning pot 2403, the cleaning water is discharged from the nozzle 1601 and by retracting the piston 1617, the cleaning water is sucked into the nozzle 1601; in this way, the interior of each nozzle 1601 can be cleaned. The cleaning water may be discharged into the cleaning pot 2403 or the drain trench 2405. Preferably, the cleaning water is discharged into the drain trench 2405 in order to keep the interior of the cleaning pot 2403 clean. The cleaning water may be sucked in and discharged in one or more cycles. The cleaning water discharged from the nozzles 1601 and the cleaning water overflowing the cleaning pots 2403 flow through a drain hole 2409 in the bottom of the drain trench 2405 to collect in a suitable drain tank (not shown) provided outside the cleaning tank 2401. Cleaning of the nozzles 1601 is not the sole function of the cleaning tank 2401 and it can also be used for other purposes such as diluting the reaction products with pure water.

EXAMPLE

Figure 16:
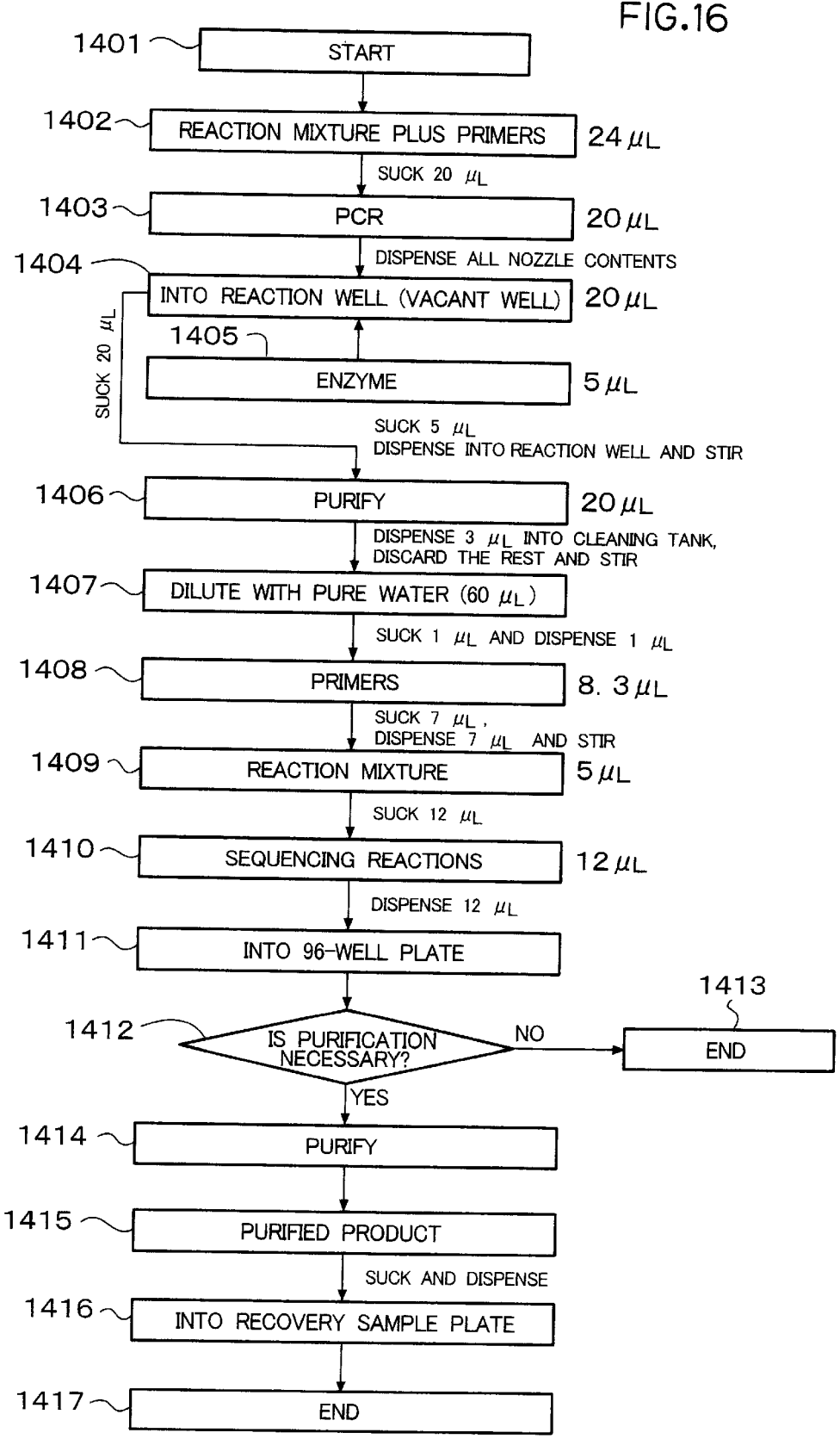
FIG. 16 is a flowchart for the steps in the process of performing PCR and sequencing reactions by the apparatus of the invention for automated preparation of DNA samples.

FIG. 16 is a flowchart for the sequence of steps in a process by which DNA samples labelled with a single fluorescent dye are prepared with the apparatus of the invention for preparing DNA samples. The process gets started in step 1401. At this stage, the apparatus of the invention for preparing DNA samples is fully prepared for the making of DNA samples by being equipped with all necessary materials and devices such as enzyme solutions, cleaning water and microtiter plates. Thus, the transport robot 26 picks up a supply plate 30 from the plate stacker 28 and places it in the plate holding section 20. In step 1402, the reactor 16 is moved to the position of the plate holding section 20 and lowered down so that a nozzle 1601 sucks 20 $\mu$L out of 24 $\mu$L of the reaction mixture plus primers that are within the well in the plate 30 which is located at coordinate (1,1). In subsequent step 1403, the reactor 16 is moved to the nozzle sealing section 22 and lowered down to seal the tip of the nozzle with paraffin and carry out PCR; after predetermined thermal cycles are completed, the paraffin seal is removed. In step 1404, the nozzle is moved to the empty well in the plate which is located at coordinate (1,2) and all contents of the nozzle are dispensed into this empty well. In step 1405, the nozzle sucks in 5 $\mu$L of purifying decomposition enzymes and adds them to the contents of the well provided in step 1404. The nozzle sucks in 20 $\mu$L of the resulting mixture. Subsequently, in step 1406, the nozzle tip is sealed with paraffin and the nozzle is heated so that the unreacted residues (dNTP and primers) in the mixture are purified by enzymatic decomposition. In step 1407, 3 $\mu$L of the purified product is dispensed into a cleaning pot 2403 and the rest discarded. Thereafter, 60 $\mu$L of pure water is forced into the cleaning pot to dilute the purified product. In step 1408, 1 $\mu$L of the dilution is sucked into the nozzle and added to the primers in the well at coordinate (2,1) to make a total of 8.3 $\mu$L. In step 1409, 7 $\mu$L of the primer mixture in the well (2,1) is sucked into the nozzle and all added to 5 $\mu$L of the reaction mixture in the well (2,2); the resulting mixture is fully agitated. In step 1410, 12 $\mu$L of the resulting mixture is sucked into the nozzle, whose tip is sealed with paraffin for sequencing reactions. After the end of sequencing reactions, the paraffin seal is removed. In step 1411, 12 $\mu$L of the mixture is dispensed into each well in a fresh 96-well plate. In step 1412, determination is made as to whether the sequencing reaction product should be purified. If the answer is negative, the sequence goes to step 1413 and the transport robot 26 replaces the 96-well plate in a predetermined tray in the plate stacker 28, whereupon the sequence of the necessary steps ends. If purification is necessary, the sequence goes to step 1414 and the necessary purification is performed not with the apparatus of the invention but with Model SG-8GC of PSS. The purified product is obtained in step 1415. The purified product is sucked into the nozzle and in step 1416 it is dispensed into a predetermined well in a recovery sample plate. Thereafter, the sequence goes to step 1417 and the transport robot 26 replaces the recovery sample plate in a predetermined tray in the plate stacker 28, whereupon the sequence of the necessary steps ends.

In the flowchart shown in FIG. 16, a single fluorescent dye is used to label DNA samples but this is not the sole case of the invention and more than one fluorescent dye may be used to label DNA samples. The process is the same except on the following points: the total volume prepared in step 1408 is increased to 16 $\mu$L; in step 1409, 4 $\mu$L of the reaction mixture is added to make a total of 20 $\mu$L which is used in sequencing reactions in step 1410.

Figure 17:
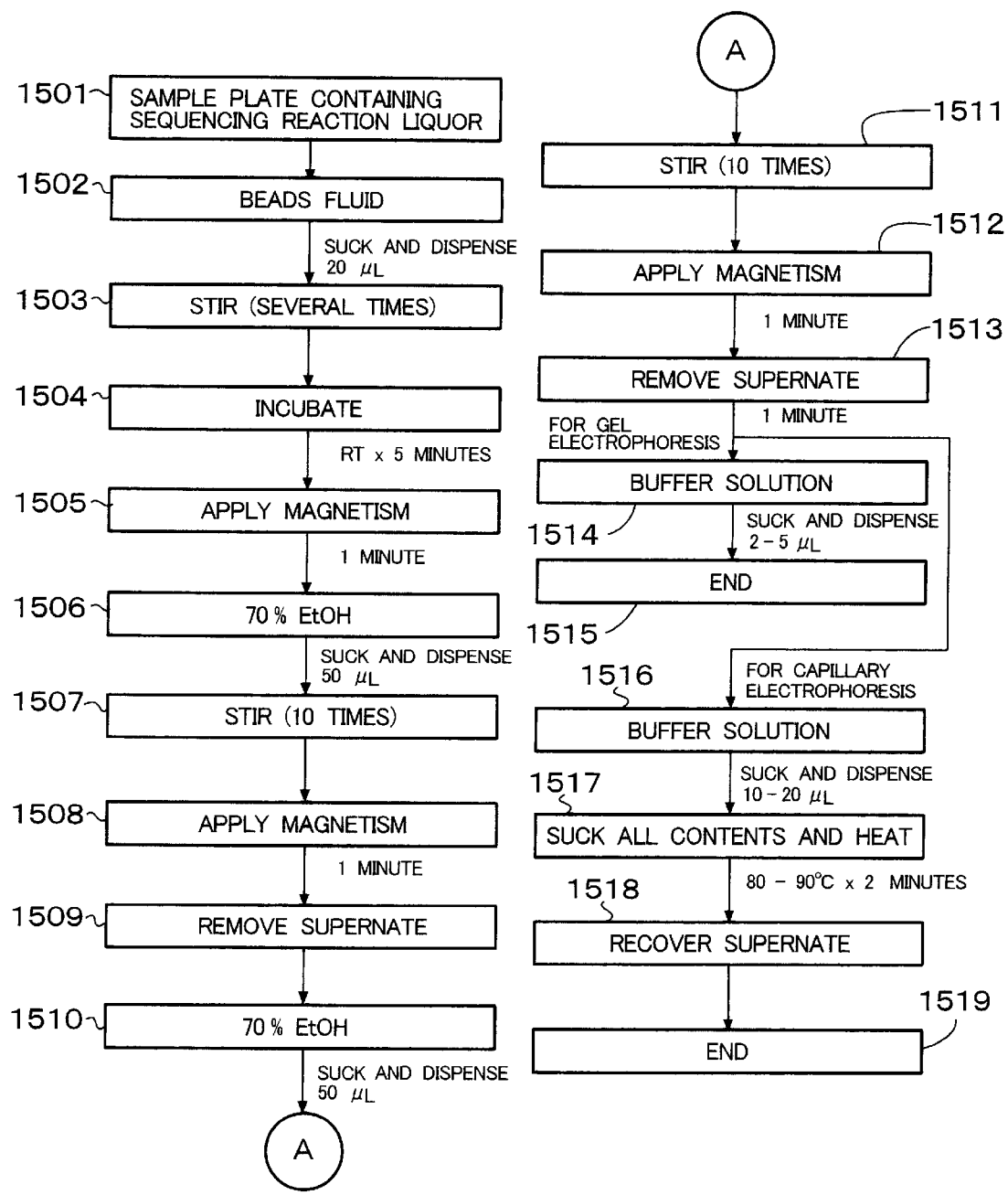
FIG. 17 is a flowchart for an exemplary process of purification that is performed in step 1414 in the flowchart of FIG. 16.

FIG. 17 is a flowchart for performing purification (see step 1414 in FIG. 16) by Model SG-8GC of PSS. The process starts with step 1501 using a sample plate containing the liquid products of sequencing reactions. This sample plate is the same as the 96-well plate used in step 1411 in FIG. 16. In step 1502, a beads fluid is added and the resulting mixture is sucked in and dispensed in 20 $\mu$L. The dispensed mixture (20 $\mu$L) is stirred several times in step 1503, incubated at room temperature for 5 minutes in step 1504, given magnetism and left standing for 1 minute in step 1505. In step 1506, 70% ethyl alcohol is added and the resulting mixture is sucked in and dispensed in 50 $\mu$L. The dispensed mixture is stirred 10 times in step 1507. In step 1508, magnetism is applied again and the mixture is left standing for 1 minute. In step 1509, the supernate is removed. In step 1510, 70% ethyl alcohol is added again and the resulting mixture is sucked in and dispensed in 50 $\mu$L. In step 1511, the dispensed mixture is stirred 10 times. In step 1512, magnetism is applied again and the mixture is left standing for 1 minute. In step 1513, the supernate is removed. The subsequent process depends on whether the purified product obtained in step 1513 is subjected to gel electrophoresis or capillary electrophoresis. If it is to be subjected to gel electrophoresis, the sequence goes to step 1514, in which a buffer solution is added to the purified product and the resulting mixture is sucked in and dispensed in ca. 2–5 $\mu$L in a fresh 96-well plate. The purification process ends in step 1515. If the purified product is to be subjected to capillary electrophoresis, the sequence goes to step 1516, in which a buffer solution is added to the purified product and the resulting mixture is sucked in and dispensed in ca. 10–20 $\mu$L. In step 1517, all contents of the well are sucked in and heated at 80–90° C. for 2 minutes. In step 1518, the supernate is recovered. The purification process ends in step 1519.

As will be apparent from the foregoing description, the present invention provides an integrated system by which PCR and sequencing reactions can be performed with a single unit of apparatus and this allows for fully automated preparation of DNA samples for use in DNA sequencing. As a result, the throughput of DNA sample preparation is significantly improved.

What is claimed is:

1. An apparatus for automated preparation of DNA samples which comprises a reactor for preparing DNA samples and adjacent thereto an enzyme supply section, a plate holding section, a nozzle sealing section and a cleaning tank section, and wherein plates are loaded onto or unloaded from said plate holding section by means of a transport robot.

2. The apparatus according to claim 1, wherein said reactor for preparing DNA samples is supported on a unidirectionally moving mechanism to be capable of moving up and down and comprises a plurality of hollow electroconductive nozzles, hollow syringes coupled to said nozzles and pistons inserted into said syringes, the top of each of said pistons having a piston head secured thereto such that it can move up and down independently of said reactor for preparing DNA samples, the intermediate portions of said electroconductive nozzles being encased in a housing having an opening on both sides, a cooling mechanism being provided adjacent one of said openings, and electroconductive boards being connected to the intermediate portions of the electroconductive nozzles within said housing and also connected to a power supply via conductors.

3. The apparatus according to claim 2, wherein said nozzles are formed of an electroconductive metal material selected from the group consisting of stainless steel, copper, aluminum, gold and platinum, and said nozzles are coated with Teflon on both inner and outer surfaces.

4. The apparatus according to claim 2, wherein said nozzles are used as reaction vessel for PCR and sequencing reactions.

5. The apparatus according to claim 4, wherein each of said nozzles has an outside diameter of 1.27 mm, an inside diameter of 0.8 mm, an overall length of 100 mm and an internal volume of ca. 60 µL.

6. The apparatus according to claim 2, wherein said electroconductive boards are spaced apart by a distance of 46 mm and said nozzles are 96 in number.

7. The apparatus according to claim 2, wherein said cooling mechanism is a cooling fan and which further includes at least one straightening plate between said two electroconductive boards for straightening the air flows created by said cooling fan.

8. The apparatus according to claim 7, wherein openable shutters are provided at the openings on both sides of said housing and said cooling fan is provided adjacent one of said shutters.

9. The apparatus according to claim 1, wherein said enzyme supply section comprises a rectangular container with an open top having a plurality of enzyme supply pots erected in the interior, a closed enzyme tank coupled monolithically to said rectangular container, a solution transfer mechanism for transferring an enzyme solution from said enzyme tank to said enzyme supply pots, and a cooling means provided on the underside of said rectangular container.

10. The apparatus according to claim 1, wherein said nozzle sealing section has at least a paraffin-filled tray and a heating/cooling means provided on the underside of said tray.

11. The apparatus according to claim 10, wherein said heating/cooling means is a Peltier device and which further includes a heat sink bonded to the side of said Peltier device which is remote from the side bonded to said tray.

12. The apparatus according to claim 1, wherein said nozzle sealing section comprises a mat formed of a heat-resistant, flexible, elastic and non-conductive material and said nozzle is sealed by pressing its tip onto the surface of said mat.

13. The apparatus according to claim 12, wherein said mat is formed of a material selected from the group consisting of fluoroplastics, fluororubbers, urethane rubber, silicone rubber and chloroprene rubber.

14. The apparatus according to claim 12, wherein said mat is either sheet-fed or a web of continuous sheet.

15. The apparatus according to claim 1, wherein said cleaning tank section comprises a cleaning tank which is a rectangular container with an open top having a plurality of cleaning pots erected in the interior and which has drain trenches adjacent said cleaning pots, said cleaning pots being supplied with cleaning water from the bottom, and said drain trenches communicating with a drain hole.

16. A reactor for preparing DNA samples which comprises a plurality of hollow electroconductive nozzles, hollow syringes coupled to said nozzles and pistons inserted into said syringes, the top of each of said pistons having a piston head secured thereto such that it can move up and down independently of said reactor for preparing DNA samples, the intermediate portions of said electroconductive nozzles being encased in a housing having an opening on both sides, a cooling mechanism being provided adjacent one of said openings, and electroconductive boards being connected to the intermediate portions of the electroconductive nozzles within said housing and also connected to a power supply via conductors.

17. The reactor according to claim 16, which is supported on a unidirectionally moving mechanism to be capable of moving up and down and wherein said piston head can move up and down independently of said reactor.

18. The reactor according to claim 16, wherein said nozzles are formed of an electroconductive metal material selected from the group consisting of stainless steel, copper, aluminum, gold and platinum, and said nozzles are coated with Teflon on both inner and outer surfaces.

19. The reactor according to claim 16, wherein said nozzles are used as reaction vessel for PCR and sequencing reactions.

20. The apparatus according to claim 19, wherein each of said nozzles has an outside diameter of 1.27 mm, an inside diameter of 0.8 mm, an overall length of 100 mm and an internal volume of ca. 60 µL.

21. The reactor according to claim 16, wherein said electroconductive boards are spaced apart by a distance of 46 mm and said nozzles are 96 in number.

22. The reactor according to claim 16, wherein said cooling mechanism is a cooling fan and which further includes at least one straightening plate between said two electroconductive boards for straightening the air flows created by said cooling fan.

23. The reactor according to claim 22, wherein openable shutters are provided at the openings on both sides of said housing and said cooling fan is provided adjacent one of said shutters.

24. The reactor according to claim 16, which is used together with an enzyme supply unit, a nozzle sealing unit and a cleaning unit.

25. The reactor according to claim 24, wherein said enzyme supply section comprises a rectangular container with an open top having a plurality of enzyme supply pots erected in the interior, a closed enzyme tank coupled monolithically to said rectangular container, a solution transfer mechanism for transferring an enzyme solution from said enzyme tank to said enzyme supply pots, and a cooling means provided on the underside of said rectangular container.

26. The reactor according to claim 24, wherein said nozzle sealing section has at least a paraffin-filled tray and a heating/cooling means provided on the underside of said tray.

27. The reactor according to claim 26, wherein said heating/cooling means is a Peltier device and which further includes a heat sink bonded to the side of said Peltier device which is remote from the side bonded to said tray.

28. The reactor according to claim 24, wherein said nozzle sealing section comprises a mat formed of a heat-resistant, flexible, elastic and non-conductive material and said nozzle is sealed by pressing its tip onto the surface of said mat.

29. The reactor according to claim 28, wherein said mat is formed of a material selected from the group consisting of fluoroplastics, fluororubbers, urethane rubber, silicone rubber and chloroprene rubber.

30. The reactor according to claim 28, wherein said mat is either sheet-fed or a web of continuous sheet.

31. The reactor according to claim 24, wherein said cleaning tank section comprises a cleaning tank which is a rectangular container with an open top having a plurality of cleaning pots erected in the interior and which has drain trenches adjacent said cleaning pots, said cleaning pots being supplied with cleaning water from the bottom, and said drain trenches communicating with a drain hole.

* * * * *